United States Patent
Lauman et al.

(10) Patent No.: US 7,107,837 B2
(45) Date of Patent: Sep. 19, 2006

(54) CAPACITANCE FLUID VOLUME MEASUREMENT

(75) Inventors: Brian Lauman, Clearwater, FL (US); Pete Hopping, Lutz, FL (US); Rick Kienman, Tampa, FL (US); Shahid Din, Palm Harbor, FL (US); Robert W. Childers, New Port Richey, FL (US)

(73) Assignees: Baxter International Inc., Deerfield, IL (US); Baxter Healthcare S.A., Wallisellen (CH)

( * ) Notice: Subject to any disclaimer, the term of this patent is extended or adjusted under 35 U.S.C. 154(b) by 0 days.

(21) Appl. No.: 10/054,487

(22) Filed: Jan. 22, 2002

(65) Prior Publication Data
US 2003/0136189 A1 Jul. 24, 2003

(51) Int. Cl.
G01F 23/26 (2006.01)
(52) U.S. Cl. ............................... 73/304 C; 73/232
(58) Field of Classification Search ............ 73/304 C, 73/149, 168, 861, 861.04, 232, 262, 263, 73/290 R
See application file for complete search history.

(56) References Cited

U.S. PATENT DOCUMENTS

| | | | |
|---|---|---|---|
| 3,375,716 A | 4/1968 | Hersch | |
| 3,428,828 A | 2/1969 | Korzekwa et al. | |
| 3,730,183 A | 5/1973 | Goldsmith et al. | |
| 3,903,478 A | 9/1975 | Stuart et al. | |
| 4,064,550 A | 12/1977 | Dias et al. | |
| 4,126,132 A | 11/1978 | Portner et al. | |
| 4,137,168 A | 1/1979 | Perrot | |
| 4,142,524 A | 3/1979 | Jassawalla et al. | |
| 4,240,408 A | 12/1980 | Schael | |
| 4,530,759 A | 7/1985 | Schal | |
| 4,586,920 A | 5/1986 | Peabody | |
| 4,784,576 A | 11/1988 | Bloom et al. | |
| 4,823,552 A | 4/1989 | Ezell et al. | |
| 4,850,805 A | 7/1989 | Madsen et al. | |
| 4,872,813 A | 10/1989 | Gorton et al. | |
| 5,135,485 A * | 8/1992 | Cohen et al. | 604/67 |
| 5,431,626 A | 7/1995 | Bryant et al. | |
| 5,542,919 A | 8/1996 | Simon et al. | |
| 5,563,584 A | 10/1996 | Rader et al. | |
| 5,569,190 A * | 10/1996 | D'Antonio | 604/72 |
| 5,609,572 A * | 3/1997 | Lang | 604/22 |
| 5,628,908 A | 5/1997 | Kamen et al. | |
| 5,634,896 A | 6/1997 | Bryant et al. | |
| 5,635,962 A * | 6/1997 | Goldis | 347/7 |
| 5,945,831 A | 8/1999 | Sargent et al. | |

(Continued)

FOREIGN PATENT DOCUMENTS

DE 2017112 10/1971

(Continued)

Primary Examiner—Hezron Williams
Assistant Examiner—Rodney Frank
(74) Attorney, Agent, or Firm—Joseph P. Reagen; Bell, Boyd & Lloyd

(57) ABSTRACT

A fluid volumetric pumping system has a fluid pump and capacitor plates disposed around a pump chamber of the fluid pump. The capacitance between the capacitor plates changes as the volume of fluid in the pump chamber changes. An electrical circuit measures a change in the capacitance between the plates and outputs a signal indicative of the volume of fluid in the pump chamber. The pump having the capacitance sensor of the present invention fluidly connects to a patient. In an embodiment, a peritoneal dialysis system provides dialysate to the patient via the pump, and the capacitance sensor measures the volume of dialysate supplied to and drained from a peritoneal cavity of the patient.

59 Claims, 7 Drawing Sheets

U.S. PATENT DOCUMENTS

| | | |
|---|---|---|
| 6,017,194 A | 1/2000 | North, Jr. |
| 6,017,198 A | 1/2000 | Traylor et al. |
| 6,122,972 A | 9/2000 | Crider |
| 6,207,522 B1 * | 3/2001 | Hunt et al. ............... 438/393 |
| 6,210,368 B1 * | 4/2001 | Rogers .................... 604/131 |
| 6,280,408 B1 * | 8/2001 | Sipin ....................... 604/65 |
| 6,426,861 B1 * | 7/2002 | Munshi .................... 361/312 |
| 6,542,350 B1 * | 4/2003 | Rogers .................... 361/284 |
| 6,562,012 B1 * | 5/2003 | Brown et al. ............. 604/253 |
| 6,932,786 B1 * | 8/2005 | Giacomelli et al. ....... 604/6.08 |
| 2003/0036719 A1 * | 2/2003 | Giacomelli et al. ....... 604/5.04 |

FOREIGN PATENT DOCUMENTS

| | | |
|---|---|---|
| EP | 0 282 323 A2 | 9/1988 |
| WO | WO 00/31553 | 6/2000 |
| WO | WO 00/44018 | 7/2000 |

* cited by examiner

CAPACITANCE FLUID VOLUME MEASUREMENT

BACKGROUND OF THE INVENTION

The present invention generally relates to devices that sense fluid and measure volumes of fluid. More specifically, the present invention relates to sensors that measure fluid volumes, preferably medical fluids, for example, fluids used during dialysis therapy.

Due to disease, insult or other causes, a person's renal system can fail. In renal failure of any cause, there are several physiological derangements. The balance of water, minerals and the excretion of daily metabolic load is no longer possible in renal failure. During renal failure, toxic end products of nitrogen metabolism (urea, creatinine, uric acid, and others) can accumulate in blood and tissues.

Kidney failure and reduced kidney function have been treated with dialysis. Dialysis removes waste, toxins and excess water from the body that would otherwise have been removed by normal functioning kidneys. Dialysis treatment for replacement of kidney functions is critical to many people because the treatment is life saving. One who has failed kidneys could not continue to live without replacing at least the filtration functions of the kidneys. Hemodialysis and peritoneal dialysis are two types of dialysis therapies commonly used to treat loss of kidney function.

Peritoneal dialysis uses a dialysis solution or dialysate, which is infused into a patient's peritoneal cavity. The dialysate contacts the patient's peritoneal membrane in the peritoneal cavity. Waste, toxins, and excess water pass from the patient's bloodstream through the peritoneal membrane and into the dialysate. The transfer of waste, toxins, and water from the bloodstream into the dialysate occurs by diffusion and osmosis because there is an osmotic gradient across the peritoneal membrane. The spent dialysate is drained from the patient's peritoneal cavity to remove the waste, toxins and water from the patient. New dialysate replaces the spent dialysate and the process repeats.

During dialysis therapy, a dialysis fluid exchange generally includes draining spent dialysis fluid from the peritoneal cavity and filling the peritoneal cavity with fresh dialysate. Keeping track of the amounts or volumes of dialysis solution drained from and supplied to the peritoneal cavity is important for proper dialysis therapy. A typical amount of dialysate solution drained from and supplied to the peritoneal cavity of an adult during an exchange can be roughly two to three liters. Dialysis fluid exchanges have been performed manually, usually by the patient, or automatically, by an automated dialysis machine.

Manually performed dialysate exchanges require that the patient or other person performing the exchange manually drain the proper amount of fluid from the peritoneal cavity and manually supply the proper new amount of fluid to the peritoneal cavity. Errors in the amount of fluid exchanged can occur when relying on manual fluid exchanges. If it is desired to know the cumulative amount of fluid used over multiple exchanges, the cumulative total fluid must be tracked manually.

So-called continuous flow peritoneal dialysis ("CFPD") systems that purport to provide continuous dialysate flow exist. In these systems, "spent" dialysate (waste laden dialysate) from the patient collects in a drain bag, which is discarded, or which runs into a household or other drain. A patient typically fills the peritoneal cavity with up to three liters of dialysate in one treatment. As a consequence, known CFPD dialysis treatments require a large amount of fresh dialysate, which must be tracked or calculated.

Automated dialysis machines use one or more fluid pumps to perform the dialysate exchanges, i.e., the pump pumps spent dialysate fluid out of the peritoneal cavity during the drain mode and pumps dialysate into the cavity during the fill mode. Known automated dialysis machines have measured and controlled the amount of fluid drained and filled during an exchange. One Automated Peritoneal Dialysis ("ADP") system uses a reference chamber and Boyle's Law to determine the volume of fluid pumped.

Another known method of measuring the volume of fluid used during dialysis treatment is weighing the fluid with a scale. In preparation for filling of the peritoneal cavity, a bag of dialysate is placed on a scale and the weight is recorded. After fluid is removed from the bag (supplied to the peritoneal cavity) the weight of the remaining fluid in the bag is read and recorded. The volume of fluid supplied to the patient can be determined from the reduced weight of the bag of fluid. Similarly, during the draining of the patient, a weight increase of the bag of fluid is used to determine the volume of fluid removed from the peritoneal cavity. Weighing the fluid to determine fluid volume requires a scale and a bag or other reservoir to be placed on the scale.

Another known method of measuring the volume of fluid pumped by a pump is simply by knowing the volume of the pump chamber and assuming that the chamber completely fills upon each pump stroke. The volume of fluid pumped is thereby determined by counting the number of pump strokes and multiplying the number by the volume of the pump chamber.

However, it is frequently the case that the pump chamber does not completely fill with fluid. For example, air can be present in the pump chamber or the pump may simply not complete a full stroke. Accordingly, the measurement of the amount of fluid pumped may be inaccurate, for example, less fluid may be actually pumped than the amount calculated. These drawbacks can become more pronounced over many pump strokes, such as when a smaller pump requires numerous pump strokes to fill or empty the peritoneal cavity.

The accuracy of measuring fluid volume pumped can become more difficult when the size of the pump chamber is small and the pump is operated through many pump strokes. For example, certain dialysis systems must pump two to three liters of dialysate into the peritoneal cavity with a pump having an inner volume of about ten to fifteen milliliters. Numerous pump strokes, about two-hundred strokes of a completely filled pump chamber, are required to pump the two to three liters of dialysate. If the pump chamber is not precisely and consistently filled or emptied with dialysate for each pump stroke, the total amount of dialysate pumped over the total number of pump strokes may be inaccurately measured.

Accordingly a need exists for devices that can accurately measure pumped fluid volume.

SUMMARY OF THE INVENTION

The present invention generally relates to new fluid sensors and fluid volume measurement devices. The sensors and measuring devices are non-invasive and provide new methods of sensing and measuring medical fluid volumes. The sensors or measuring devices can be used in many types of medical operations, and are particularly suitable for dialysis, such as hemodialysis and peritoneal dialysis, including continuous flow peritoneal dialysis.

To this end, in an embodiment of the invention, a device for measuring a volume of medical fluid is provided. The device includes a plurality of capacitor plates of fixed spacing. In an embodiment, the capacitor plates form at least one opposing pair. A medical fluid receptacle is positioned between the pair of capacitor plates. A circuit electrically connects to the pair of capacitor plates. The circuit has an output indicative of the volume of the medical fluid when the fluid is in the fluid receptacle.

In an embodiment, the medical fluid receptacle further comprises a pump chamber having at least one fluid port. The pump chamber is positioned between the pair of capacitor plates.

In an embodiment, the pump chamber further comprises at least one flexible membrane wall movable to pump medical fluid.

In an embodiment, the device also includes or operates with a pump piston in fluid pumping relationship relative to the pump chamber. One of the capacitor plates of the pair moves with the pump piston.

In an embodiment, the medical fluid receptacle further includes first and second flexible membrane walls. At least one of the first and second membrane walls can move to change a volume within the receptacle.

In an embodiment, the medical fluid receptacle further includes a portion of a disposable dialysis fluid flow path useable with a dialysis machine.

In an embodiment, the capacitor plates can be planer or non-planer in shape or a combination of both. The shape can be substantially the same as the receptacle when full and/or the same as a portion of a pump chamber.

In an embodiment, the circuit may further includes a ground connection to one capacitor plate of the pair and a voltage sensor connected to the other capacitor plate of the pair.

In an embodiment, the device includes a guard that electrically protects at least a portion of a signal from the capacitor plates.

In an embodiment, the device includes a voltage source that enables a voltage proportional to the capacitance between the plates to be generated.

In a further embodiment of the present invention a system for measuring a volume of a fluid to or from a patient is provided. The system includes a fluid receptacle fluidly connected to a patient. First and second capacitor plates are provided, between which a variable dielectric is created depending on an amount of the fluid in the fluid receptacle. An electrical circuit connects to the capacitor plates. The circuit outputs a signal based on the variable dielectric. The signal is indicative of the volume of the fluid in the fluid receptacle.

In an embodiment, the fluid receptacle operates inside of a fluid pump chamber.

In an embodiment, the fluid receptacle is positioned between the first and second capacitor plates.

In an embodiment, the system includes a pump piston. One of the first and second capacitor plates defines an aperture that allows a portion of the piston to extend outside the plate.

In an embodiment, the system includes a pump piston, and one of the first and second capacitor plates is a portion of the pump piston.

In an embodiment, the system includes a displacement fluid that expands and contracts the fluid receptacle to fill and empty the fluid in and out of the receptacle.

In an embodiment, the capacitor plate effectively moves with the expanding fluid within the receptacle.

In an embodiment, the fluid receptacle has a variable volume and can be sucked against a pump chamber that is adapted to draw a vacuum on the receptacle.

In an embodiment, at least one of the first and second capacitor plates is movable and shaped like the receptacle when the receptacle is fill. The capacitor plates can also be shaped like a pump housing.

In an embodiment, the fluid receptacle includes a disposable cassette. At least one wall of the cassette includes a flexible membrane.

In an embodiment, the system includes a processor or controller that determines a volume of the fluid from the signal outputted by the electrical circuit.

In an embodiment, the system includes a controller that determines a cumulative volume of fluid from a plurality of individual volumes of fluid in the fluid receptacle.

In still another embodiment of the present invention, a system for measuring a volume of a fluid to be provided to or from a patient is provided. The system includes a fluid receptacle fluidly connected to a patient. First and second capacitor plates are provided. An electrical circuit connects to the capacitor plates. The circuit outputs a signal based on a variable dielectric between the plates. The signal can also be based on a changing distance of one or both of the plates and a changing surface area of one or both the plates. The signal is indicative of the volume of the fluid in the fluid receptacle.

In an embodiment, at least one of the capacitor plates has a varying surface area.

In an embodiment, the signal outputted by the electrical circuit is electrically guarded by a voltage that tracks the signal, wherein the voltage is applied to a guard that shields the signal.

Moreover, in another embodiment of the present invention, a dialysis system is provided. The system includes a fluid flow path. A fluid receptacle fluidly connects to the fluid flow path. A capacitance sensor is positioned relative to the fluid receptacle. The capacitance sensor is capable of measuring a volume of fluid in the receptacle.

In an embodiment, the capacitance sensor uses a pulsed voltage and measures the amount of voltage that builds up during the pulse.

In an embodiment, the fluid receptacle is part of a disposable set for dialysis therapy.

In another embodiment of the present invention, a method of measuring a volume of a medical fluid pumped by a fluid pump is provided. The method includes sensing a first state of a fluid receptacle with capacitance plates when the medical fluid receptacle is substantially empty of fluid. Next, the medical fluid is provided to the fluid receptacle. Then, a second state of the fluid receptacle is sensed with the capacitor plates when the fluid receptacle is substantially full of medical fluid. Further, a volume of the medical fluid in the fluid receptacle is determined based on the first and second states sensed by the capacitance plates.

In an embodiment, the method further includes substantially emptying the fluid receptacle of fluid, providing medical fluid to the receptacle, sensing another second state and determining another volume of the medical fluid.

In an embodiment, the method includes continuously sensing the state of the fluid receptacle as the fluid enters the receptacle.

In an embodiment, the method includes determining a total volume of fluid from a plurality of volumes of medical fluid provided to the receptacle.

In an embodiment, the method includes positioning the capacitor plates at opposing sides of a pump chamber.

In still another embodiment of the present invention, a method of providing dialysis to a patient needing same is provided. The method includes measuring a volume of dialysis fluid with a capacitance sensor and passing the volume of the dialysis fluid into a portion of a patient.

In an embodiment, the portion includes a peritoneal cavity of the patient.

In an embodiment, the method includes infusing the measured fluid volume into a sleeping patient.

In an embodiment, the method includes infusing the measured fluid into the patient at nighttime.

In yet another embodiment of the present invention, a method of providing continuous flow peritoneal dialysis to a patient is provided. The method includes passing a volume of dialysis fluid through a pair of capacitor plates to measure the volume, urging the volume of fluid into a portion of a patient and recirculating the volume of fluid from the patient to clean the fluid.

In an embodiment, passing the volume of fluid through the pair of capacitor plates and urging the volume of fluid into the portion of the patient occurs simultaneously at a fluid pump.

Further still, in another embodiment of the present invention, a method of operating a system that displaces a medical fluid is provided. The method includes moving the medical fluid from a first location to a second location and measuring a volume of the fluid moved by a capacitance sensor.

In an embodiment, the method includes the step of delivering the medical fluid to a patient.

In an embodiment, the method includes controlling an amount of the medical fluid provided to the patient by measuring the volume of fluid with the capacitance sensor.

In an embodiment, the method includes visually indicating the amount moved or the amount pumped to a patient or operator.

It is therefore an advantage of the present invention to provide an improved medical fluid volume measurement system.

Another advantage of the present invention to provide an improved system for providing dialysis treatment.

An advantage of the present invention is to provide volume measurement systems and methods for use in continuous flow peritoneal dialysis treatment.

Another advantage of the present invention is to provide improved methods of measuring medical fluid volumes.

A further advantage of the present invention is to provide non-invasive fluid volume measurement.

Still another advantage of the present invention is to provide capacitance fluid sensing and fluid volume measurement devices and methods.

Still a further advantage of the invention is to provide accurate fluid volume measurement for a fluid pump over numerous pump strokes.

Yet another advantage of the invention is to provide accurate fluid volume measurement for a fluid pump when the pump chamber is not completely filled with or emptied of fluid.

Furthermore, an advantage of the present invention is to provide improved methods of providing dialysis.

Yet a further advantage of the present invention is to provide a proportional fluid volume sensing system that provides a proportional output, whereby partially full volume measurements can be obtained.

Additional features and advantages of the present invention are described in, and will be apparent from, the following Detailed Description of the Invention and the figures.

DETAILED DESCRIPTION OF THE INVENTION

The present invention provides medical fluid volume sensors, systems for performing medical treatments using the medical fluid volume sensors, and methods pertaining to same. The present invention particularly provides fluid volume sensors, systems and methods that can be used for peritoneal dialysis treatment and with peritoneal dialysis systems. One such peritoneal dialysis system is a continuous flow peritoneal dialysis system which continuously and simultaneously infuses and drains dialysate to and from a patient's peritoneal cavity. The peritoneal dialysis system, and thus the present invention, can be connected to a dual lumen catheter implanted in the peritoneal cavity, or other multi-lumen patient access, for example.

It should be noted, however, that the present invention can be used for a variety of medical treatments as well as a variety of dialysis systems and methods. For example, the present invention can be used in hemodialysis. Likewise, the principles and methods of the present invention can also be used for sensing medical fluids in non-dialysis applications.

The present invention can measure the volume of fluid provided to or removed from a patient. The fluid volume sensing and measuring apparatus and method of the present invention is a non-invasive measurement system. That is, the present invention can measure the volume of a fluid without contacting or extending into the fluid. The system uses capacitance measurement techniques to determine the volume of a fluid inside of a chamber.

As the volume of the fluid changes, a sensed voltage that is proportional to the change in capacitance changes. Therefore, the sensor can determine whether the chamber is, for example, empty, an eighth full, quarter full, half full, full, or any other percent full. Each of these measurements can be made accurately, for example, at least on the order of the accuracy achieved by known gravimetric scales or pressure/volume measurements. The present invention, however, is simpler, non-invasive, inexpensive and does not require the medical operation to be a batch operation.

Figure 1A:
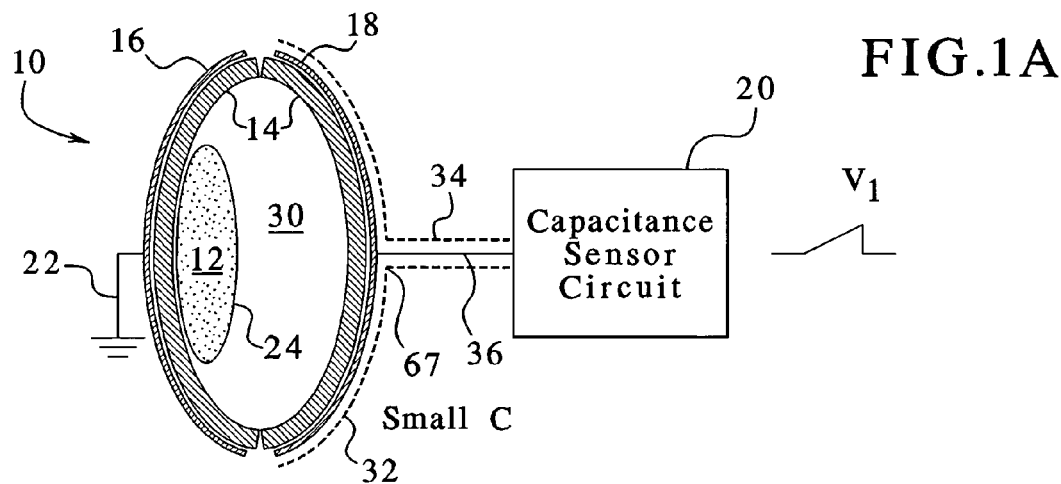
FIGS. 1A, 1B and 1C are schematic diagrams showing a fluid volume sensor of the present invention having various fluid volumes.
Figure 1B:
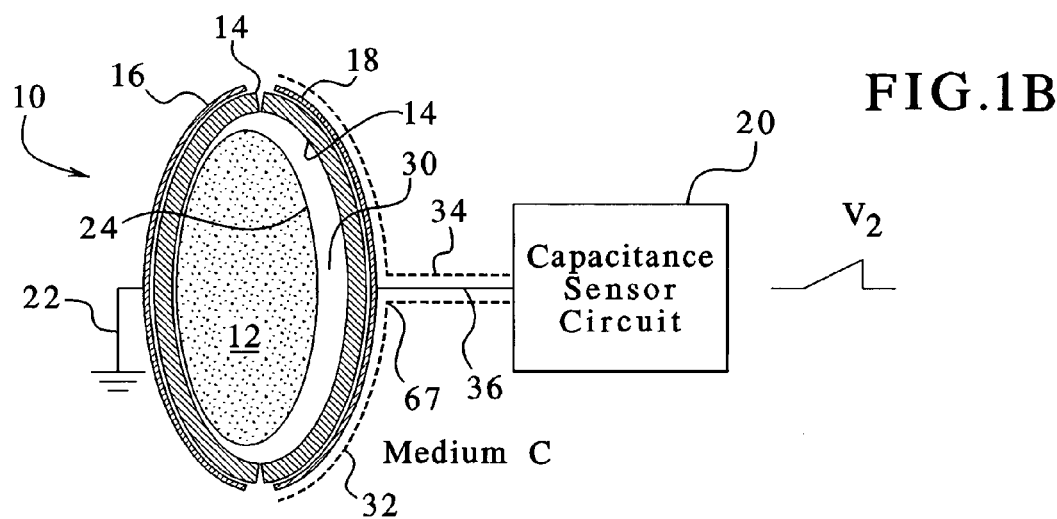
Figure 1C:
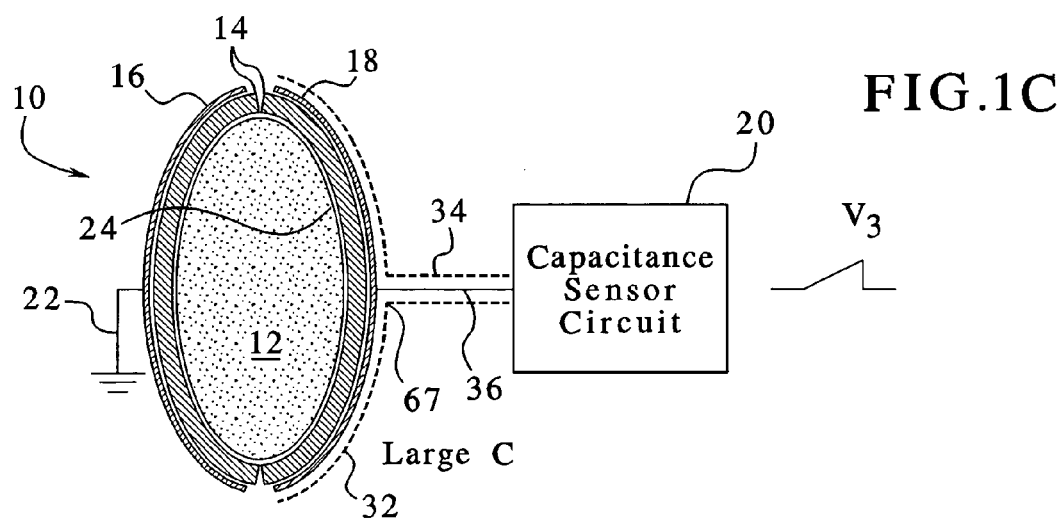

One fluid volume sensor or measurement device 10 is shown schematically in FIGS. 1A, 1B and 1C. FIG. 1A shows the sensor 10 having virtually no amount of fluid 12 in a fluid container 14. The container 14, in an embodiment, is plastic or some other material having a relatively low dielectric constant, similar to that of air. As illustrated, the container 14 includes two clamshell type plates. The ends of the plates allow a medical fluid, such as dialysate, to enter the container 14. It should be appreciated however that the container 14 can be of any number of different pieces including a solid piece. The container 14 can define any sort of aperture or apertures for enabling entry and exit of a volume of medical fluid.

FIG. 1B shows the fluid container 14 having a greater volume of fluid 12 than the fluid 12 in the container 14 of FIG. 1A. FIG. 1C shows the fluid container 14 substantially full of the fluid 12. In an embodiment, the fluid container 14 is rigid, however, the container 14 could also be flexible or have flexible components. In an embodiment, at least part of the container 14 is included in a disposable cassette for transferring medical fluid, for example, dialysate. As part of the disposable cassette, the container 14 can be integrated with a pump, wherein the container 14 becomes the pump chamber.

The fluid 12 is maintained between a flexible membrane receptacle 24, which provides an enclosed and sterile passageway for the medical fluid. In an embodiment, the container provides part of a pump chamber for the medical fluid as described in detail below. However, the container 14 does not have to be part of an actively pumped chamber and can alternatively be a passive chamber.

The fluid volume sensor 10 includes first and second capacitor plates 16 and 18 positioned at opposite sides of and outside of the fluid container 14. The capacitor plates are of a conductive material or metal. The metal capacitor plates do not contact the fluid 12 or the sterile disposable membrane 24 and are instead isolated from same by the container 14.

The fluid 12 of the fluid container 14 is positioned between the first and second capacitor plates 16 and 18. Although the term "plate" is used throughout the present specification, the plates, as illustrated do not have to be flat. The capacitor plates 16 and 18 can have any desired shape and construction. As illustrated herein, the capacitor plates 16 and 18, in an embodiment, have non-planer shapes that substantially conform to the shape of the fluid container 14 (and devices operably connected to the container 14 such as a pump piston head). The shapes also substantially conform to the shape of the receptacle 24 when the receptacle expands to be full or substantially full.

In FIGS. 1A to 1C, the dielectric constant of the fluid 12 is much higher than the dielectric constant of the fluid 30, which in an embodiment is air. For instance, a water based fluid 12 may have a dielectric constant that is around eighty times that of air.

Because of the large disparity between dielectric values, the expanding volume of the fluid 12 effectively moves the capacitor plate 16, adjacent to the high dielectric fluid 12 towards the plate 18. In this manner, the capacitance between the plates 16 and 18 changes depending on the relative positions between the expanding surface of the fluid 12 and capacitor plate 18. That is, as the volume of the fluid 12 in the fluid container 14 changes, the capacitance between the plates 16 and 18 also changes, as described in more detail below.

The fluid volume sensor 10 includes a capacitance sensor circuit 20, which electrically couples to the active metal or otherwise conductive capacitor plate 18. The sensor 10 maintains a ground connection 22 to the ground capacitor plate 16. The capacitance sensing circuit 20 electrically couples to the capacitor plate 18 via a signal line 36. The signal line 36 transmits a signal from the active plate 18 to the capacitance sensor circuit 20. The sensor circuit 20 outputs a voltage that is proportional to the fluid 12 in the fluid container 14, as figuratively indicated by the heights, V1, V2, V3, of the voltage ramps associated with each of the FIGS. 1A to 1C, respectively.

The fluid volume sensor 10, in an embodiment, includes an electrical guard 67. The purpose of the electrical guard 67 is to protect the voltage sensed by the active plate 18, which moves along the signal line 36. The capacitance produced across the plates 16 and 18 in an embodiment is on the order of Picofarads. Consequently, the signal line 36 from the plate 18 to the circuit 20 is highly susceptible to outside capacitance produced by neighboring electrical components and from the surrounding area in general.

The guard 67 has a plate portion 32 and a line portion 34. That is, the guard protects the capacitance signal from the capacitor plate 18, all the way along the signal line 36, to the capacitance sensor circuit 20. The plate portion 32, in an embodiment, is a conductive metal shell that is electrically insulated from and that electrically insulates the capacitor plate 18. The line portion 34 in an embodiment is the surrounding metal in a coaxial cable. In operation, the plate portion 32 and the line portion 34 of the guard 67 are maintained at the same potential as the signal from the active capacitor plate 18, wherein the guard 67 shields the signal line 36 from being influenced by external signals, electric fields or other grounds.

In FIG. 1A, the fluid container 14 is substantially empty of fluid 12. By "substantially empty" the fluid container 14 can be completely empty or contain a small amount of fluid 12 relative to a substantially filled container 14 of FIG. 1C. The capacitance of the sensor 10 with the fluid 12 between the plates 16 and 18 is at a particular value due at least in part to the absence of fluid 12 within the container 14.

The capacitance sensor circuit 20 of the sensor 10 measures the voltage across the metal or otherwise conductive capacitor plates 16 and 18 to produce the graphically illustrated voltage V1. The capacitance C1 across plates 16 and 18 in FIG. 1A is proportional to 1/V1. The capacitance of FIG. 1A and the inversely proportional voltage V1 indicate a substantially empty fluid container 14.

As an external or integral source adds fluid 12 to the fluid container 14, the membrane receptacle 24 in the fluid container 14 fills and expands as illustrated in FIG. 1B. The expanding edge of the membrane receptacle 24 filled with the high dielectric fluid 12 becomes the functional equivalent of the ground capacitance plate 16. When the volume of liquid 12 within the container 14 increases, the volume of a displacement fluid 30, such as air, filling the remainder of the container 14 necessarily decreases. The capacitance, C, changes according to the function $C=k\times(S/d)$, wherein k is the dielectric constant determined by the dielectric property of the material between two plates, S is the surface area of the individual plates and d is the distance between the plates 16 and 18.

As a source moves the fluid 12 in and out of the container 14, the volume of fluid 12 continuously changes. The membrane receptacle 24 filling with fluid 12 can form differing shapes due to the change in volume, the effects of gravity, etc. The surface area, S, of the above function can change due to the expanding membrane receptacle 24, which acts as the functional equivalent of the capacitor plate 16. The distance, d, of the above function can also change due to the expanding volume of the fluid 12 within the membrane receptacle 24. It should be appreciated that as the volume of fluid 12 in the membrane receptacle 24 of the container 14 expands, the area, S, of the plate 16, if it changes, increases and the distance, d, between the plates 16 and 18, if it changes, decreases, both of which cause the capacitance C in the above function to increase (and the output voltage of the circuit 20 to proportionally drop).

As the fluid 12 in the membrane receptacle 24 of the container 14 increases from FIG. 1A to FIG. 1B, the capacitance between the plates 16 and 18 also increases. According to the above-explained relationship between capacitance and voltage, the voltage across the plates 16 and 18 likewise drops. This is schematically illustrated by the voltages V1 and V2, respectively, of FIGS. 1A and 1B. Since measured voltage V2 is less than measured voltage V1, the capacitance C2 is proportional to the capacitance C1 by a factor of V1/V2. That is, the change in voltage is inversely proportional to the change in capacitance.

Likewise, FIG. 1C shows that the fluid 12 has expanded the membrane receptacle 24 to virtually reach the inner volume of the container 14. By "substantially full" the fluid container 14 can be completely full of fluid 12 or have a large amount of fluid 12 compared to being substantially empty as in FIG. 1A. The output voltage V3 of FIG. 1C is indicative of the substantially full volume of fluid 12 in the fluid container 14.

The change in capacitance, while possibly being related to the change in distance, d, between the plates 16 and 18 and the change in surface area, S, of the membrane receptacle 24, is in no doubt due at least in part to the change in dielectric constant k as the low dielectric fluid 30 is replaced by the high dielectric fluid 12. The reason for the change in capacitance between the plates 16 and 18 and the exact contribution that the three variables of the simple plate capacitance equation, C=k×(S/d), have on the capacitance, C, is influenced by the complex geometries and non-ideal dielectrics. More importantly, the capacitance changes can be calibrated as follows: (i) the capacitance change can be measured by the potential along the signal line 36; and (ii) different voltages can be correlated to different signal volumes of fluid 12 within the membrane receptacle 24 of the container 14.

It should be appreciated that knowing the signal potential when the container 14 is empty and the voltage when the container 14 is full, that any intermediate voltage can be correlated to a percentage loading or percentage volume of fluid 12. There can be a hysteresis effect in which different paths will be taken (on a graph of voltage versus volume of fluid 12) from empty to full and from full to empty, however, the hysteresis effect can either be accounted for in software or eliminated through circuitry.

It should also be appreciated that any intermediate voltage can also be correlated to a percentage volume of dielectric fluid 30, i.e., air. Thus, the capacitance sensor 10 of the present invention can also be used to detect the presence of air within the receptacle 24. For instance, if the receptacle 24 is expected to be in a full or substantially full state at a certain time, but the sensor 10 only indicates a half-full state, the system of the sensor 10 can determine that the receptacle 24 has entrapped air and can calculate the percentage of same. This is a desirable feature for fluid delivery systems, wherein the delivery system occasionally needs to purge entrained air.

FIGS. 1A to 1C illustrate a general embodiment, wherein the container 14 defines any type of volume or chamber, etc., in which fluid 12 expands and contracts within a membrane receptacle 24. Any device for expanding and contracting the membrane receptacle 24 with fluid 12 could be employed and may or may not be integrated with the container 14. Also, in another embodiment, the membrane receptacle 24 can be omitted.

The capacitor plates 16 and 18 may be provided in a substantially parallel, opposing manner or may have another opposing, non-parallel geometry. Further, more than two capacitor plates may be employed and more than one signal may be generated.

Figure 2:
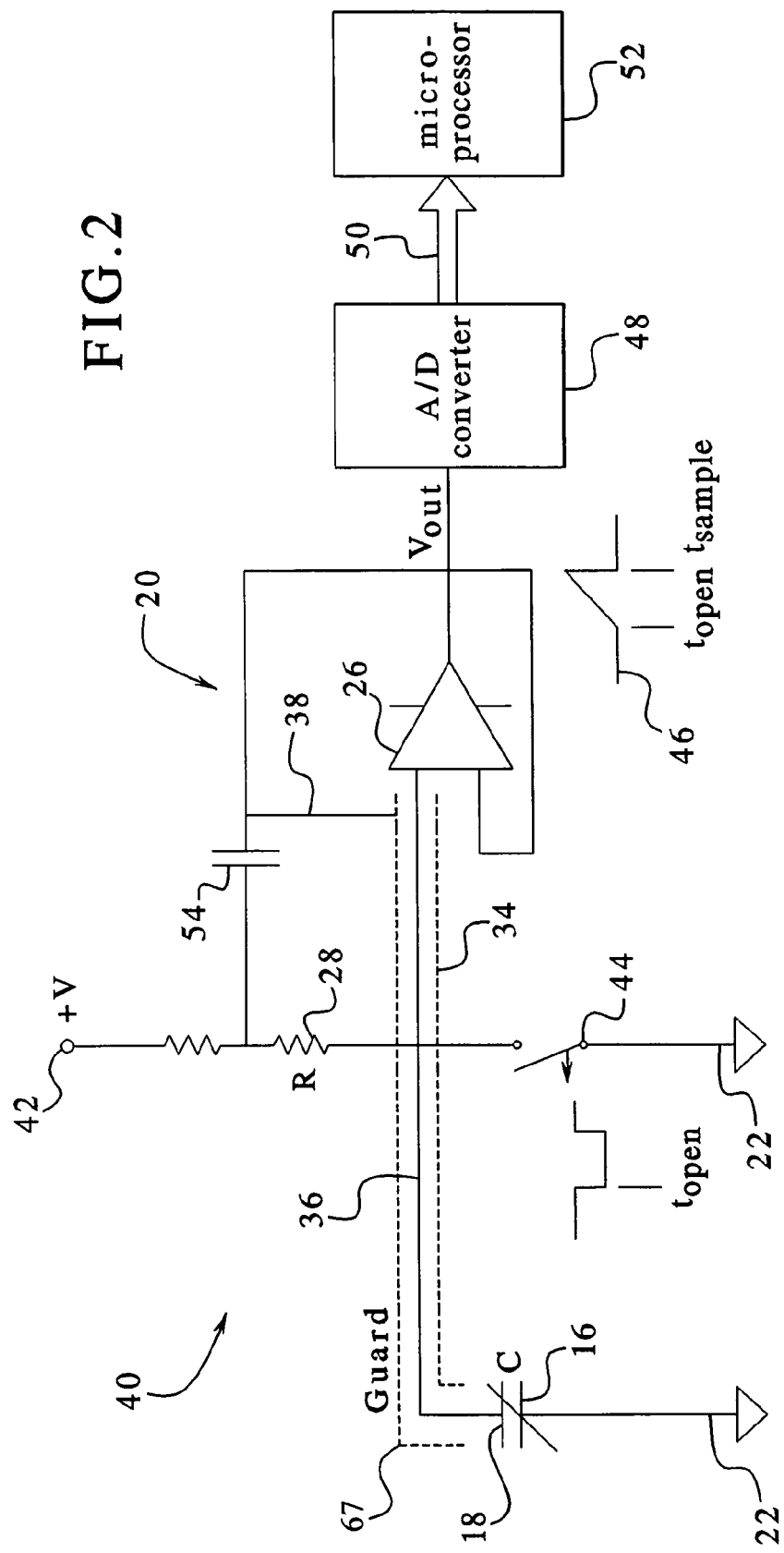
FIG. 2 is a schematic diagram illustrating one embodiment of a capacitance sensor circuit of the present invention.

FIG. 2 illustrates an embodiment of a system circuit 40 that takes into account the capacitance sensor circuit 20, the signal line 36, the guard 67, the active capacitor plate 18 electrically coupled to the signal line 36, and the ground capacitor plate 16 electrically coupled to ground 22, as described above. The capacitance sensor circuit 20 includes an amplifier 26 that electrically couples to signal line 36, wherein the signal line 36 transmits the electrical potential from the active capacitor plate 18.

The signal along signal line 36 is a high impedance signal that is very susceptible to external signals produced by other electrical components and by the environment in general. The amplifier 26 amplifies the signal from signal line 36 to produce a low impedance output, $v_{out}$. The amplified low impedance output, $v_{out}$, is fed back around via loop 38 to the line portion 34 of the guard 67. In this manner, the system circuit 40 continuously maintains the same electrical potential along the guard 67 and the signal line 36.

The capacitance sensor circuit 20 of the system circuit 40 includes a voltage source 42. In an embodiment, voltage source 42 supplies 5 VDC, however, voltage source 42 can supply other suitable voltages. The capacitance sensor circuit 20 of the system circuit 40 also includes a switch 44. When the switch 44 is closed, the voltage supplied by voltage source 42 shunts to ground. That is, when the switch 44 is closed, amplifier 26 outputs virtually no potential and $v_{out}$ is effectively zero.

When the switch 44 opens, $v_{out}$ increases over time as indicated by the ramp 46 (FIGS. 1A to 1C show similar ramps culminating in voltages V1 to V3, respectively). The sampled voltage, $v_{out}$, varies proportionally to the function 1/(R×C), where R is a constant value of the resistor 28 and C is the varying capacitance across the active plate 18 and ground plate 16.

It should be appreciated that eventually, if given enough time, $v_{out}$ would rise to equal the voltage, +V, of voltage source 42. The amount of time depends on the capacitance. If the capacitance, C, is relatively low (container 14 relatively devoid of fluid 12 and full of low dielectric fluid 30), $v_{out}$ rises to +V in a relatively short amount of time. If the capacitance is relatively high (container 14 relatively full of fluid 12 and devoid of low dielectric fluid 30), $v_{out}$ rises to +V over a relatively longer period of time.

The corollary of this is that over a fixed amount of time, $t_{open}$ to $t_{sample}$, which is less than the time needed for $v_{out}$ to rise to +V when capacitance C is low, $v_{out}$ will rise to some voltage less than +V, depending on the capacitance C. In this manner, measured $v_{out}$ is proportional to the overall capacitance created across the high dielectric fluid 12, for example, dialysate, and the low dielectric fluid 30, for example, air. Again, hysteresis will affect the value of $v_{out}$ depending upon whether the overall capacitance is increasing (container 14 filling with fluid 12) or whether the overall capacitance is decreasing (container 14 losing fluid 12).

The gain or value of resistor 28 affects the dynamics of the system and must be chosen based on the value of the voltage source 42 and the range of the capacitance values generated across plates 16 and 18. In one embodiment, the values of the resistor 28 and the voltage source 42 are chosen so that $v_{out}$ spans a repeatable and detectable range between zero volts and +V, over the range of capacitance values from empty to full. In an embodiment, the range of capacitance is approximately 2 to 60 Picofarads and the resistance of resistor 28 is in the range of 50 to 150 kΩ. These values can obviously be varied and are provided only to show one possible implementation of the present invention.

The signal, $v_{out}$, is an analog signal that varies as the capacitance, C, between plates 16 and 18 changes. An analog to digital converter 48 converts signal, $v_{out}$, to a digital signal 50. The digital signal 50 is then provided to a microprocessor 52. The microprocessor 52 stores data that enables a % full (of fluid 12) or volume of fluid 12 to be generated. The microprocessor 52 sums multiple digital signals 50 over time. For instance, the microprocessor 52 sums multiple fill and discharge cycles of a pump (e.g., a dialysate pump chamber can be on the order of fifteen milliliters and the patient can require around two liters of dialysate). The microprocessor 52 can determine the total volume of medical fluid 12 pumped or otherwise transferred to a patient or signal an end to a session upon reaching a predetermined total value.

In any type of medical or dialysis system, the present invention enables the display of the volume and/or the flowrate of fluid that depends on the volume to a patient or operator. The microprocessor 52, in an embodiment, sequences an internal timer that opens the switch 44 at $t_{open}$, allowing the capacitance sensor plate 18 to charge until the time $t_{sample}$ when the signal, $v_{out}$, is measured. In a typical embodiment, the switch would close at some time after $t_{sample}$. The microprocessor 52 can additionally include filtering software that averages multiple digital signals 50 and/or senses and eliminates false signals.

The capacitance sensor circuit 20 of the system circuit 40, in an embodiment, includes various features to prevent external signals from corrupting the true signal along signal line 36. For instance, the circuit 20 can employ "bootstrapping" techniques, which are well known in the art, to guard the signal line 36 from capacitance values associated with other components within the circuit. For example, the switch 44 can have an associated capacitance value that would influence the capacitance along the signal line 36. The bootstrapping technique, which is similar to the guard technique feedback loop 38, would negate the effects from any capacitance developing across the switch 44.

The capacitance sensor circuit 20 in an embodiment can include other electrical components for enhancing the accuracy and stability of the system circuit 40. The functions of these components are well known to those of skill in the art. For example, the capacitor 54 is a "bootstrap" device that helps to maintain the linearity of ramp 46. Various electrical components (not illustrated) may also be added to enhance the performance of the system circuit.

The above described circuits and mode of operation can be implemented in a variety of different fluid container configurations. FIGS. 1A to 1C illustrate an embodiment, wherein the container 14 does not necessarily correspond to a pumping chamber.

Figure 3:
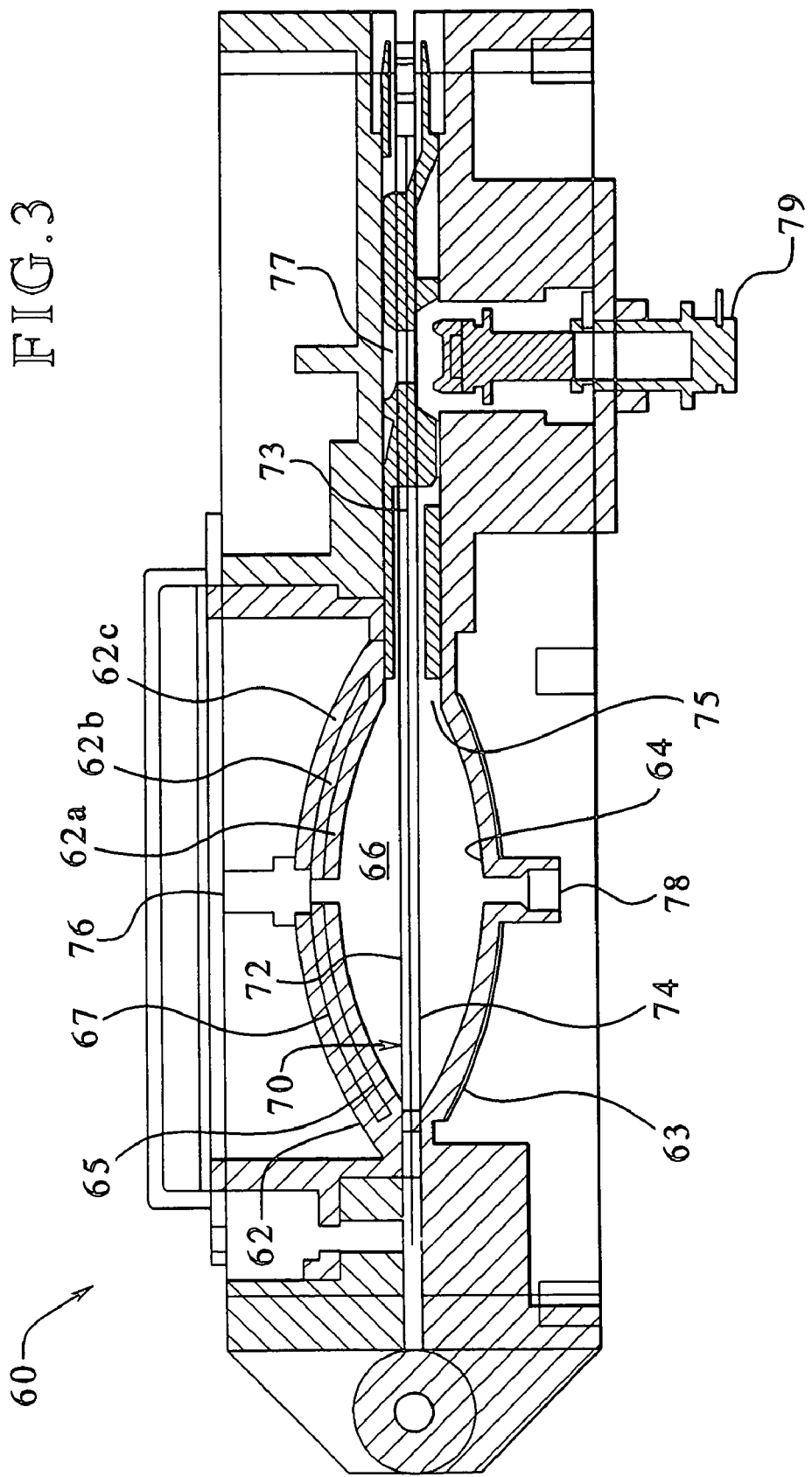
FIG. 3 is a sectional view of a fluid volume sensor according to another embodiment of the present invention, wherein the sensor is placed in combination with a pneumatically or hydraulically driven pump.

Referring now to FIG. 3, a sensor 60 of the present invention correlates a change in the capacitance to a volume of medical fluid within a pump chamber 66. That is, the container in this embodiment is a pump chamber.

The sensor 60 includes a "clamshell" design having first and second portions 62 and 64, which together form the pump chamber 66. In an embodiment, the portions 62 and 64 form a rigid, fixed volume, disked shaped, pump chamber 66 of known volume. The volume of the chamber 66 can be calculated or determined by a calibration process. The volume of chamber 66 can then be programmed into a microprocessor, such as the processor 52 of FIG. 2.

The clamshell first and second portions 62 and 64 are closed and sealed on a disposable and expandable membrane receptacle 70. The disposable receptacle 70 includes two flexible membranes 72 and 74. The flexible membranes of the present invention my be made of any suitable material compatible with the fluid to be pumped, for example, inert plastic or rubber material. One or more fluid pathways 73 (e.g., valved passageways of a dialysis disposable) fluidly communicate with an opening or aperture 75 defined between the first and second portions 62 and 64 and the flexible membranes 72 and 74.

The one or more pathways 73 enable medical fluid, for example, dialysate, to enter and exit the chamber 66 between the membranes 72 and 74 of the receptacle 70. In an embodiment, the one or more fluid pathways 73 lead to a manifold 77, wherein the manifold operably communicates with a series of valves 79 that open and close the fluid pathways 73, according to a program.

FIG. 3 shows the pump chamber 66 in an empty state with both films 72 and 74 in relaxed positions so that the flexible receptacle 70 is closed. The empty volume state is achieved when the films 72 and 74 are collapsed so that substantially all the fluid is removed from the sterile receptacle 70 and likewise the pump chamber 66.

The empty volume state can be achieved, for example, by forcing both membranes 72 and 74 together against each other or against either one of the inside of portions 62 and 64 of the pump chamber 66. The empty pump chamber state can be calibrated in this position. When the pump chamber 66 is in the full state, the medical fluid resides between the films 72 and 74 of the receptacle 70, wherein the films are pressed and/or sucked against the inside walls of portions 62 and 64 of the pump chamber 66. The full chamber volume can be calibrated in this state.

It should be appreciated that the clamshell portions 62 and 64 and the films 72 and 74 of the receptacle 70 form a diaphragm pump. Either one or both of the films 72 and 74 can be moved towards and away from the clamshell portions 62 and 64 by any suitable activation device. In various embodiments, the diaphragm pump is pneumatically, hydraulically or mechanically actuated.

The diaphragm pump of FIG. 3 is, in an embodiment, pneumatically, hydraulically or otherwise fluidly activated. That is, the pump does not require a separate piston or mechanical actuator. The clamshell portions 62 and 64 define port openings 76 and 78, respectively, to allow for movement of a displacement fluid (for example, pneumatic or hydraulic fluid) into and out of the chamber areas outside of the receptacle 70 to operate the diaphragm pump.

In an alternative embodiment, the medical fluid, for example, dialysate, is pressurized to move in and out of the pump chamber 66 between the films 72 and 74. A separate pressure source is used to force the fluid into the receptacle 70.

In a further alternative embodiment, the receptacle 70 defined by membranes 72 and 74 may be filled with medical fluid by applying negative pressures to one or both of the chamber ports 76 and 78. The medical fluid in the chamber 66 between the films 72 and 74 can be emptied by applying a positive pressure to at least one of the chamber ports 76 and 78.

In the capacitive sensor 60, the clamshell portions 62 and 64 form or hold the capacitor plates of the present invention. In an embodiment, lower clamshell portion 64 is made of an inert plastic, wherein a metal capacitor plate 63 attaches to the outer surface of the plastic clamshell portion 64. For proper sterilization, it is desirable that the metal capacitor 63 plate not directly contact the medical fluid. In an embodiment, the metal capacitor plate 63 disposed on the outside of the clamshell portion 64 electrically couples to ground.

In an embodiment, clamshell portion 62 includes an active metal or otherwise conductive capacitance plate 65 within a number of layers: inner layer 62a, middle layer 62b and outer layer 62c. Each of the layers 62a to 62c is made of an inert plastic. The active metal capacitor plate 65 resides between plastic layers 62a and 62b. A metal guard plate 67, providing noise protection to the active plate and the circuitry attaching thereto, as described above, resides between plastic layers 62b and 62c. Thus no metal is exposed to either direct contact with the dialysate or to potential human contact.

The active capacitor plate 65 of clamshell portion 62 electrically couples to a capacitance sensing circuit, such as circuit 20 described in connection with FIGS. 1A, 1B, 1C and 2). The guard plate 67 also electrically couples to the feedback loop of the capacitance sensing circuit as illustrated in the above figures.

In one implementation, a negative pressure is constantly maintained at port 78, so that the lower membrane 74 is pulled to conform to the inner surface of the grounded clamshell portion 64 during a multitude of fill and empty cycles. In this implementation, the upper membrane 72 does the pumping work. That is, when a negative pressure is applied to the port 76 of the clamshell 62, the membrane 72 sucks up against and conforms with the inner surface of the clamshell layer 62a. This action draws fluid through one of the fluid pathways 73 and the aperture or opening 75 from the manifold 77 and into the expandable receptacle 70. To expel fluid, the negative pressure is released from the port 76, wherein the membrane 72 collapses to push the fluid from the receptacle 70. Alternatively, a positive pressure is applied through port 76 in place of the negative pressure.

In operation, the receptacle 70 expands between the portions 62 and 64 (receptacle 24 expands from one side of the container 14 in FIGS. 1A to 1C). The varying distance, d, of the low dielectric displacement fluid between the expanding and contracting receptacle 70 and the portions 62 and 64 may have some effect on the capacitance between the ground plate 63 and the active plate 65. Likewise the surface area, S, defined by the ground 63 and active 65 capacitance plates and the expanding membrane 72 may have some effect on the overall capacitance. Certainly, the changing overall dielectric affects the sensed capacitance.

As the films 70 and 72 expand and fill with medical fluid, for example, dialysate, the capacitance changes, i.e., increases. Each different amount of medical fluid within the chamber 66 therefore has a unique overall capacitance. Therefore, a unique capacitance value can be associated with each specific fluid volume in the chamber, for example, substantially empty, partially full, or substantially full.

By generating a pulsed voltage over a particular and predetermined time period, the system circuit generates a high impedance potential across the active and grounded capacitor plates 65 and 63, respectively. The capacitance sensing circuit amplifies the high impedance signal to produce a low impedance potential, $v_{out}$ (also fed back to guard the capacitance signal), which varies depending on the overall volume of fluid in the chamber. The amplified potential is converted to a digital signal and fed to a microprocessor where it is filtered and/or summed and utilized to provide a volume and/or flowrate indication to a patient or operator or to control the pumping of the system, for example, to terminate dialysate flow upon reaching a total overall volume. The volume indication can be in any desired form, for example, visual, numerical, audible, electronic and combinations thereof.

It should be appreciated that the capacitor plates 65 and 63 of the portions 62 and 64, respectively (and the guard 67), conform to the shape of the fluid that expands within the receptacle 70 of the films 72 and 74. The capacitor plates 65 and 63 of the portions 62 and 64 have substantially the same shape as the receptacle 70 fully expanded with fluid. The accuracy of the sensor 60 is enhanced due to the fact that the capacitor plates 65 and 63 conform with or have substantially the same shape as the fluid container. That is, the accuracy provided by the curved capacitor plates 65 and 63 of the cupped shaped portions 62 and 64, respectively, is greater than if the plates 65 and 63 were simply straight, parallel plates.

As stated above, in connection with FIGS. 1A to 1C, the capacitor plates 63 and 65 can be, but do not have to be substantially parallel. In an alternative embodiment, more than two capacitor plates may be provided and multiple signals may be generated.

Figure 4A:
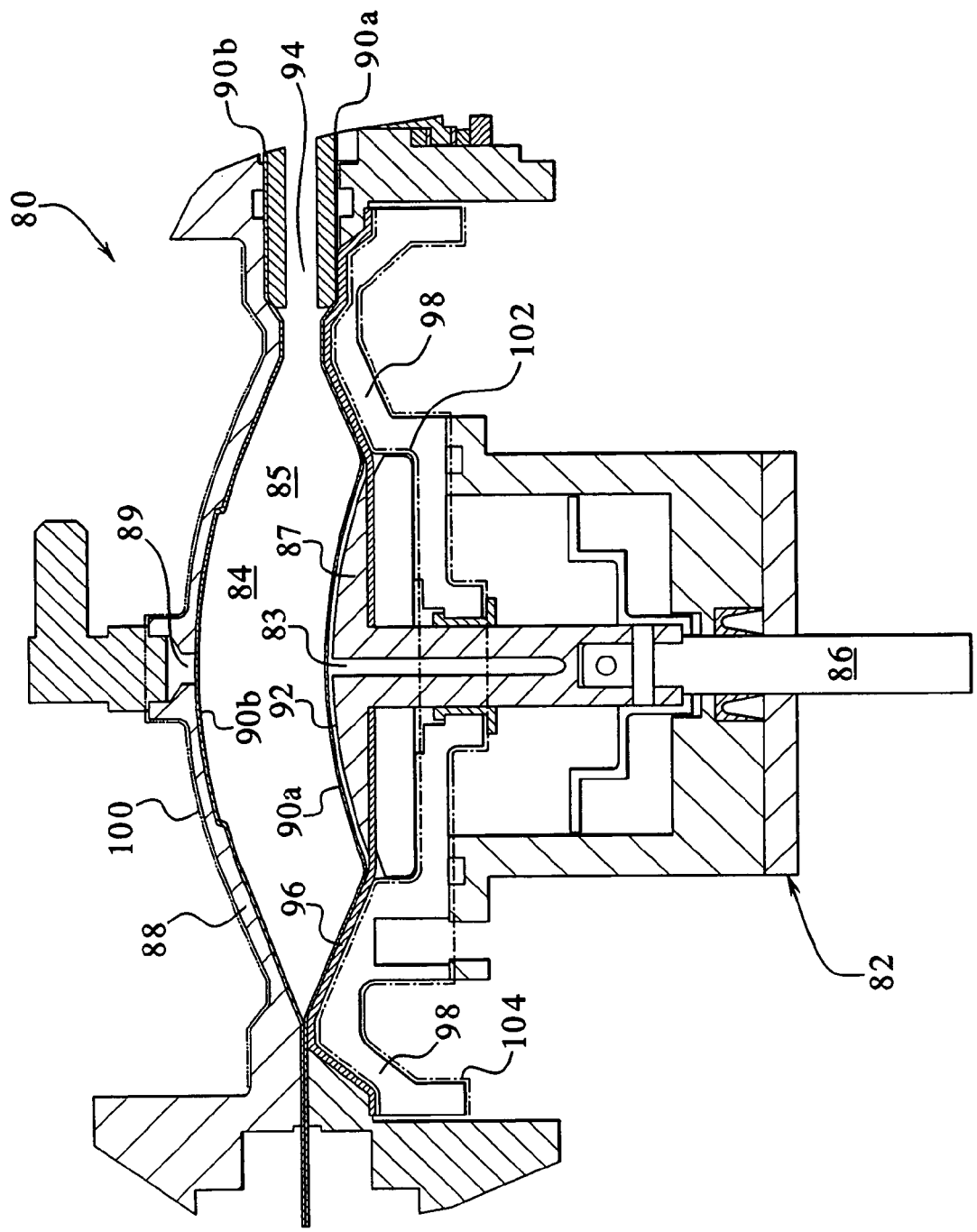
FIGS. 4A and 4B are sectional views of a fluid volume sensor according to a further embodiment of the present invention, wherein the sensor is placed in combination with a mechanically driven pump.
Figure 4B:
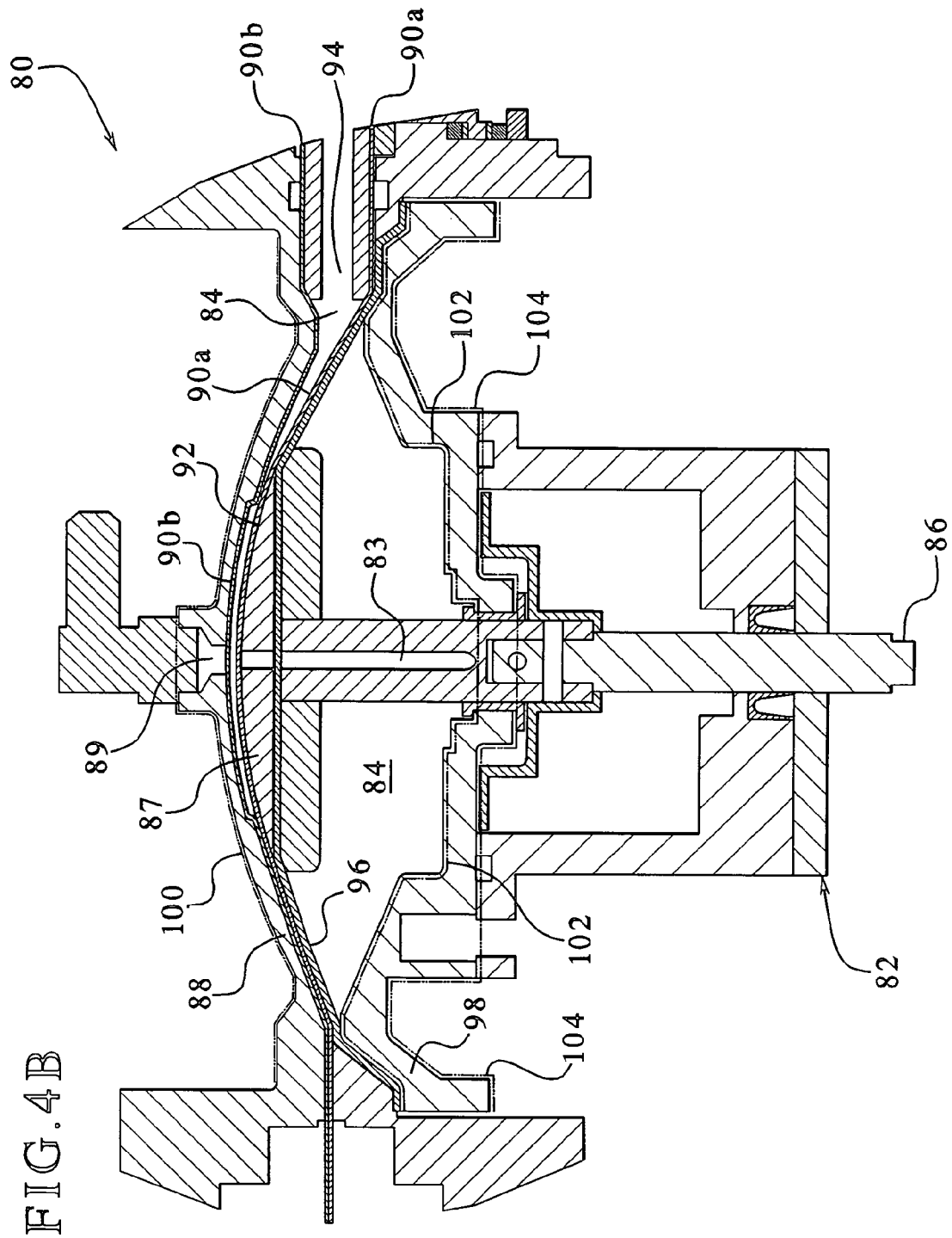

Referring now to FIGS. 4A and 4B, in another embodiment a sensor 80 of the present invention is illustrated. The sensor 80 includes a pump 82, as above. In this embodiment, however, the pump 82 is at least partially mechanically driven. The pump 82 defines a pump chamber 84 and has a pump piston 86, which includes a piston head 87. The pump chamber 84 is defined by upper, rigid pump housing member 88 and lower rigid pump housing member 98. As before, a flexible fluid receptacle 85 is defined by expandable membranes or sheets 90a and 90b, which in an embodiment form part of a disposable unit for use with a dialysis system, such as a continuous flow dialysis system.

In FIG. 4A, when the pump 82 is full of medical fluid, the pump chamber 84 and the fluid receptacle 85 have substantially the same shape. In FIG. 4B, when the pump 82 has displaced all or most all of the medical fluid, the pump chamber 84 maintains the same volume but the membranes 90a and 90b defining the fluid receptacle 85 have collapsed to virtually a zero volume.

The pump membrane 90a, in an embodiment, is adapted to seal against or be mechanically attach to a face 92 of the piston head 87 of the pump piston 86. The membrane 90b seals against or attaches to the member 88. The piston head 87 and the member 88 define ports 83 and 89, respectively, through which a vacuum can be pulled (or positive pressure applied). The ports 83 and 89 fluidly connect to channels (not illustrated) that fluidly extend radially outwardly from ports 83 and 89 in various directions. The channels help to distribute the negative pressure applied through the ports 83 and 89, so that the respective membranes 90a and 90b substantially conform to the interior shapes of the members 88 and 98 and the piston head 87 when one or more vacuum is applied to the sensor 80.

In an embodiment, negative pressure is constantly applied through the port 89 to hold the membrane 90b against the member 88 (similar to FIG. 3). The member 88 supports the ground metal or otherwise conductive capacitance plate 100. The member 98 supports the active metal or otherwise conductive capacitor plate 102 and the guard 104. The piston head 87 and the membrane 90a reciprocate towards and away from the upper pump housing member 88, for example, via a linear actuator operably connected to piston 86, a fluid actuator or any other suitable actuator.

At least one fluid port opening 94 to the receptacle 85 defined by the membranes 90a and 90b within the pump chamber 84 allows fluid to enter and exit the receptacle 85 within the pump chamber 84. During the pump fill stroke, with the membrane 90b vacuum-pressed against the member 88 and the membrane 90a vacuum-pressed against the member 98 and the piston head 87, the piston head 87 pulls the membrane 90a away from the center position in the middle of the chamber 84 to produce a negative pressure within the receptacle 85, which pulls fluid through the dialysate disposable and into the receptacle 85.

FIG. 4A shows the pump 82 of the sensor at the end of the fill stroke. During the pump empty stroke, an actuator drives the piston 86, which pushes the piston head 87 and the accompanying membrane 90a upward. The membrane 90a forces medical fluids, for example, dialysate, out through an aperture 94 defined between membranes 90a and 90b and members 88 and 98.

Other than replacing the fluid pump driving mechanism with the mechanical pump piston 86 and piston head 87, the sensor 80 operates substantially the same as the sensor 60 of FIG. 3. Both systems employ a static volume container or chamber, and a changing volume flexible receptacle that fluidly communicates with a source of fluid, for example, a dialysate bag. The flexible receptacle may be a portion of a disposable unit. Both systems have capacitor plates which conform to the shape or volume created by the receptacle, when full, and a circuit guard which conforms to the shape of the active capacitor plate.

The system 80 includes an additional substrate 96 tensioned between the upper and lower members 88 and 98, respectively. The substrate 96, defines, together with the membrane 90a, a closed volume of air with which to withdraw from the system via a negative pressure applied to the port 83 of the piston head 87. Accordingly, when a vacuum is applied to the port 83 and the piston head 87 is actuated upwardly away from the member 98, the membrane 90a remains drawn to and conformed with the shape of the additional substrate 96.

In operation, the receptacle 85 expands between the members 88 and 98. The varying distance, d, of the low dielectric displacement fluid between the expanding and contracting receptacle 85 and the lower member 98 may have some effect on the capacitance between ground plate 100 and the active plate 102. Likewise the surface area, S, of the capacitance plates and the moving membrane 90a may have some effect on the capacitance. Certainly, the changing overall dielectric affects the sensed capacitance.

As the membranes 90a and 90b expand and fill with medical fluid, for example, dialysate, the overall capacitance changes, i.e., increases. By generating a pulsed voltage over a particular and predetermined time period, the system circuit generates a high impedance potential across the grounded and active capacitor plates 100 and 102. The high impedance potential is indicative of an amount of fluid in the receptacle 85. If the potential does not change over time when it is expected to change, the sensor 80 can also indicate an amount or portion of air within the receptacle 80.

A capacitance sensing circuit amplifies the high impedance signal to produce a low impedance potential, $v_{out}$ (also fed back to the guard 104), which varies depending on the overall capacitance. The amplified potential is converted to a digital signal and fed to a microprocessor where it is filtered and or summed and utilized to visually provide a volume and/or or flowrate indication to a patient or operator or to control the pumping of the system, for example, to terminate dialysate flow upon reaching a total overall volume. Any suitable medium may be used to indicate the volume or flowrate.

Again, the capacitor plates 100 and 102 conform to the shape of the fluid that expands within the receptacle 85 of the membranes 90a and 90b. The capacitor plates 100 and 102 have substantially the same shape as the receptacle 85 fully expanded with fluid. The accuracy of the sensor 80 is enhanced due to the fact that the capacitor plates 100 and 102 conform with or have substantially the same shape as the fluid container.

As stated above, in connection with FIGS. 1A to 1C and FIG. 3, the capacitor plates 100 and 102 can, but do not have to be substantially parallel. In an alternative embodiment, more than two capacitor plates may be provided and multiple signals may be generated.

Figure 5:
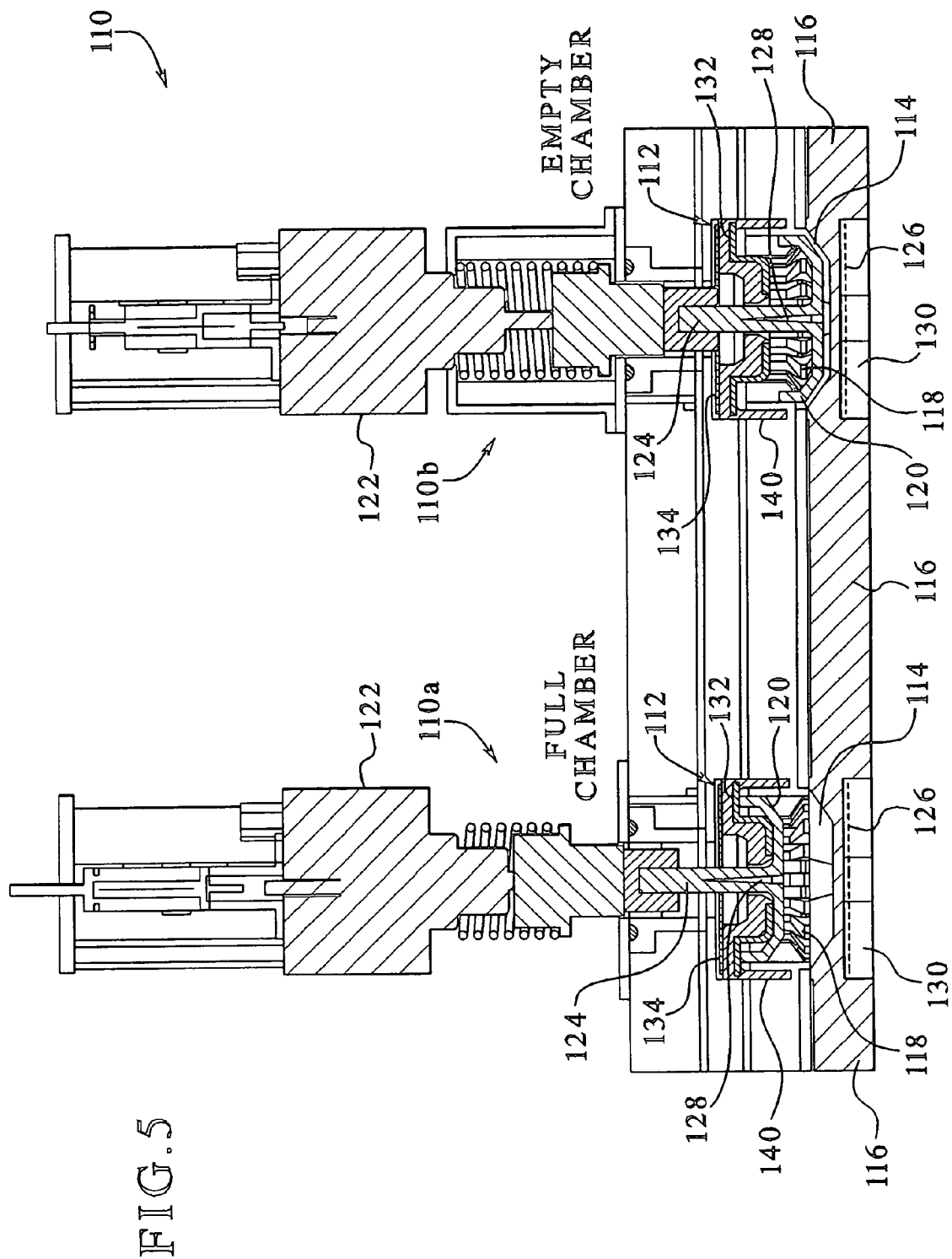
FIG. 5 is a sectional view of multiple, cooperating fluid volume sensors according to yet another embodiment of the present invention, wherein each sensor is placed in combination with a mechanically driven pump.

Referring now to FIG. 5, in a further embodiment of the present invention, a set of capacitance sensors 110a and 110b (also referred to collectively herein as sensor 110) is illustrated. FIG. 5 illustrates that the two sensors 110a and 110b cooperate. The sensor 100a on the left cooperates with a pump 112 that is currently full of medical fluid, while the sensor 110b on the right cooperates with a pump 112 that is currently empty. The pumps 112 are timed such that while one pump is filling the other is emptying. Any of the pump sensors 60, 80 or 110 disclosed herein may be operably coupled to other pump sensors. The volumes sensed in the pumps 112 are summed to produce an overall amount of medical fluid transferred to the patient.

The sensor 110 differs from the sensors 60 and 80 because the fluid receptacle 114 is defined on one side by a fixed, plastic, disposable cassette 116 and defined on the opposite side by a flexible, inert, disposable membrane 118. The previous embodiments included fixed hard plastic housings with internal flexible membranes.

The full chamber sensor 110a of FIG. 5 illustrates that the piston head 120 inverts or moves the membrane 118 away from the cassette 116 when the receptacle 114 is full of dialysate. The empty chamber sensor 110b illustrates that the piston head 120 pushes the membrane 118 into the chamber cavity defined by the cassette 116 when the receptacle 114 is empty.

As with the sensor 80, a linear actuator 122 drives a piston 124 to pump fluid in an out of the receptacle 114. Unlike the previous sensors 60 and 80, however, no vacuum is required to constantly pull a second membrane towards the grounding capacitor plate 126. A protective cover 130 is disposed at the cassette interface 116 to electrically isolate the ground metal or otherwise conductive capacitor plate 126.

A vacuum is applied through the aperture 128 defined by the piston 124 to pull and seal the membrane 118 against the piston head 120. As with any of the previous systems, the membrane 118 in alternative embodiments seals or connects to the piston head (or pump chamber wall as the case may be) via any suitable mechanical or adhesive technique.

Figure 6:
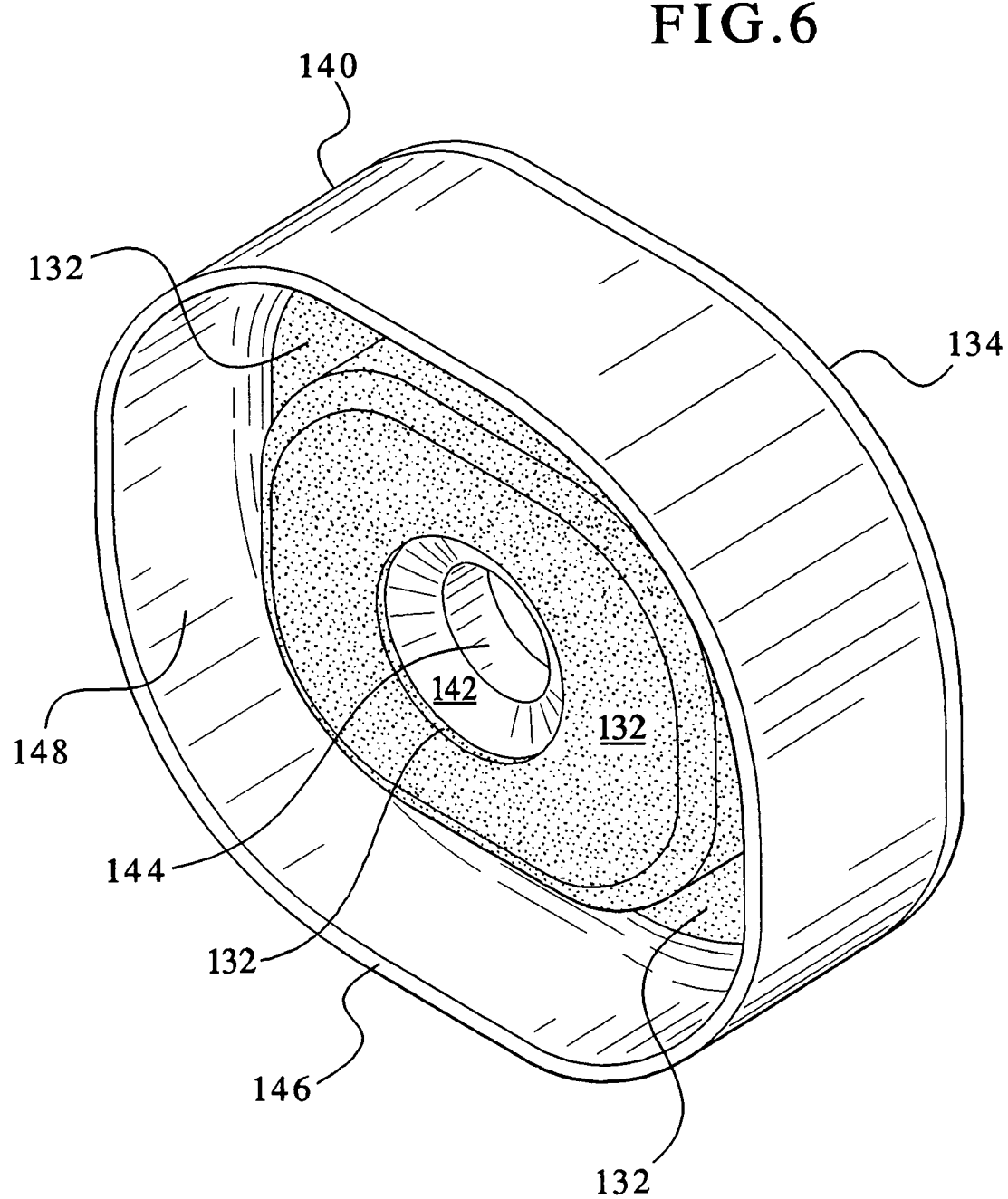
FIG. 6 is a perspective view of one embodiment of a capacitance cup of the present invention.

Referring to FIGS. 5 and 6, a capacitor cup 140, corresponding active metal or otherwise conductive capacitor plate 132 and electrical guard 134 are illustrated. The cup 140, is in an embodiment, made of an inert, rigid plastic. The cup 140 includes an integral inner portion 142 that defines an aperture 144, which enables the piston 124 to move back and forth within the cup 140, which is positionally fixed to the medical fluid system.

The electrical guard 134 fixes to the back of the cup 140. The active capacitor plate 132 affixes to the surface of the inner portion 142. In an embodiment, an inert, plastic cover (not illustrated) electrically isolates the capacitor plate 132. Alternatively, the system 110 relies on the piston head 120 to isolate the capacitor plate 132.

The cup 140 defines an outer ridge 146 that encloses the inner portion 142. The inner portion 142 and the outer ridge 146 define a continuous opening 148 that enables the piston head 120 to move back and forth within the continuous opening 148. In an embodiment, the active capacitor plate 132 follows the contour of the inner portion 142 into the opening 148 and outward along the back flange portion of the cup 140 that links the ridge 146 to the inner portion 142. The inner portion 142, back flange portion and ridge 146 can integrally form the cup 140. In other embodiments, one or more of the portions may separately attach to form the cup 140.

The capacitor sensor 110 operates substantially as described above with the systems 60 and 80. As the membrane 118 moves back and forth so that the receptacle 114 fills with and empties medical fluid, for example, dialysate, the overall capacitance changes. By generating a pulsed voltage over a particular and predetermined time period, a system circuit electrically coupled to the active plate 132 generates a high impedance potential. The high impedance potential is indicative of an amount of fluid in the receptacle 114. If the potential does not change over time when it is expected to change, the 110 sensor can also indicate an amount or portion of air within the receptacle 114.

The capacitance sensing circuit amplifies the high impedance signal to produce a low impedance potential, $v_{out}$ (also fed back to the guard 134), which varies depending on the overall capacitance. The amplified potential is converted to a digital signal and fed to a microprocessor where it is filtered and/or summed and utilized to visually provide a volume and/or flowrate indication to a patient or operator or to control the pumping of the system, for example, to terminate dialysate flow upon reaching a total overall volume. The sensor 110 can employ any suitable medium to indicate the volume or flowrate.

It should be understood that various changes and modifications to the presently preferred embodiments described herein will be apparent to those skilled in the art. Such changes and modifications can be made without departing from the spirit and scope of the present invention and without diminishing its intended advantages. It is therefore intended that such changes and modifications be covered by the appended claims.

The invention is claimed as follows:

1. A device for providing dialysis solution to a to a patient comprising:
    a fluid receptacle, the fluid receptacle having a substantially hollow interior and defining an exterior surface;
    a membrane receptacle adapted to receive dialysis solution, the membrane receptacle carried within the substantially hollow interior of the fluid receptacle;
    at least two capacitor plates positioned adjacent to the exterior surface of the fluid receptacle, the at least two capacitor plates arranged in an opposing manner;
    a circuit electrically connected to the at least two capacitor plates, the circuit configured to produce an output signal indicative of a volume of the dialysis solution in the membrane receptacle; and
    a member for providing at least a portion of the dialysis solution within the membrane receptacle to or from a patient.

2. The device of claim 1, wherein the membrane receptacle operates with a pump chamber having at least one fluid port.

3. The device of claim 2, wherein the capacitor plates have a shape that is substantially the same as the shape of the pump chamber.

4. The device of claim 1, wherein the membrane receptacle includes at least one flexible membrane wall movable to pump medical fluid.

5. The device of claim 1, wherein the membrane receptacle includes first and second flexible membrane walls, at least one of the first and second membrane walls being movable to change a volume of the receptacle.

6. The device of claim 1, wherein the membrane receptacle includes a portion of a disposable dialysis fluid flow path useable with a dialysis machine.

7. The device of claim 1, wherein at least one capacitor plate a non-planer shape.

8. The device of claim 1, wherein the capacitor plates have a shape at least substantially the same as the exterior surface of the fluid receptacle.

9. The device of claim 1, wherein the circuit charges the capacitor plates and measures a change in voltage from the capacitor plates over a time interval.

10. The device of claim 1, wherein the circuit further comprises:
    a ground connection to one of the capacitor plates; and
    a capacitance sensor circuit connected to another capacitor plate.

11. The device of claim 1, which includes a pair of substantially parallel capacitor plates.

12. A device for providing dialysis to a patient comprising:
    a plurality of capacitor plates defining a space between the plates;
    a fluid receptacle for holding a volume of dialysis fluid positioned within the space, the receptacle having a flexible membrane receptacle adapted to receive the dialysis fluid and operable to enable a relatively low dielectric fluid to be present at certain times between the receptacle and the plates;
    a circuit electrically connected to the plurality of capacitor plates, the circuit having an output indicative of the volume of dialysis fluid in the fluid receptacle; and
    a fluid line coupled to the patient to deliver at least a portion of the volume of dialysis fluid to or from the patient.

13. A device for providing continuous flow peritoneal dialysis comprising:
    a fluid receptacle;
    a flexible dialysis receptacle disposed within the fluid receptacle, the dialysis receptacle capable of being placed in fluid communication with a patient;
    first and second capacitor plates defining a space within and between which the fluid receptacle is located, the plates having a variable dielectric between the plates that is dependent on an amount of fluid in the dialysis receptacle; and
    an electrical circuit connected to the capacitor plates that creates a signal that is related to the variable dielectric.

14. A system for measuring a volume of a fluid to be provided to or from a patient, the system comprising:
    a fluid receptacle, the fluid receptacle carrying a flexible membrane receptacle capable of being fluidly connected to a patient;
    first and second capacitor plates defining a space within and between which the fluid receptacle is located, the plates having a variable dielectric between the plates that is dependent on an amount of a fluid in the flexible membrane receptacle; and
    an electrical circuit connected to the capacitor plates that creates a signal that is related to the variable dielectric.

15. The system of claim 14, wherein the signal is indicative of the volume of the fluid in the flexible membrane receptacle.

16. The system of claim 14, wherein the signal is indicative of a volume of air in the fluid receptacle.

17. The system of claim 14, wherein the signal is indicative of a portion of fluid in the flexible membrane receptacle and a portion of air in the fluid receptacle.

18. The system of claim 14, wherein the fluid receptacle operates inside of a fluid pump chamber.

19. The system of claim 18, wherein the capacitor plates have a shape substantially the same as the fluid pump chamber.

20. The system of claim 14, wherein the fluid receptacle is positioned between the first and second capacitor plates.

21. The system of claim 14, further comprising a pump piston, wherein one of the first and second capacitor plates defines an aperture that allows a portion of the piston to extend outside the plate.

22. The system of claim 14, further comprising a pump piston, wherein the pump piston moves between the capacitor plates.

23. The system of claim 14, further comprising a displacement fluid that expands and contracts the flexible membrane receptacle to fill and empty the fluid in and out of the receptacle.

24. The system of claim 14, wherein the fluid receptacle includes a pump chamber wall defining a port that can apply a negative pressure to the flexible membrane receptacle and pull at least a portion of one of the membranes towards the port.

25. The system of claim 14, wherein the fluid receptacle includes a pair of pump chamber walls each defining a port.

26. The system of claim 14, wherein at least one of the first and second capacitor plates is represented by the surface of the adjacent fluid.

27. The system of claim 14, wherein the flexible membrane receptacle is part of a disposable cassette.

28. The system of claim 14, further comprising a processor that determines a volume of the fluid from the signal outputted by the electrical circuit.

29. The system of claim 14, further comprising a processor that determines a cumulative volume of fluid from a plurality of individual volumes of fluid in the fluid receptacle.

30. The system of claim 14, wherein the pair of capacitor plates have a shape substantially the same as the receptacle when the receptacle is full of fluid.

31. A system for measuring a volume of a fluid to be provided to or from a patient, the system comprising:
a fluid receptacle;
first and second capacitor plates positioned outside of and on opposing sides of the fluid receptacle;
a flexible membrane receptacle carried within the fluid receptacle, the flexible membrane in fluid communication with the patient: and
an electrical circuit providing a voltage source that enables a signal indicative of the volume of the fluid in the receptacle to be generated.

32. The system of claim 31, wherein the output signal is based on at least one of: a variable dielectric between the plates, a changing surface area of one of the plates, and a changing distance between the plates.

33. The system of claim 31, wherein the signal is based on a varying dielectric constant between the fluid and air.

34. The system of claim 31, wherein the circuit charges the capacitor plates and measures a change in voltage from the capacitor plates over a time interval.

35. The system of claim 34, wherein the time interval is a fixed time interval.

36. A medical fluid delivery system, comprising:
a fluid flow path including a patient connection;
a membrane receptacle positioned inside a chamber, the membrane receptacle so constructed and arranged to be in fluid communication with the fluid flow path; and
a capacitance sensor positioned on opposing sides of an outer surface of the chamber and capable of accounting for an amount of a relatively low dielectric fluid existing between the membrane receptacle and the chamber to indicate a volume of fluid in the receptacle.

37. The system of claim 36, wherein the chamber is a pump chamber.

38. The system of claim 37, wherein the capacitance sensor further comprises first and second capacitor plates at opposite sides of the pump chamber.

39. The system of claim 38, wherein the capacitor plates have a shape substantially the same as part of the pump chamber.

40. The system of claim 36, wherein the capacitance sensor further comprises first and second capacitor plates positioned at opposite sides of the fluid receptacle.

41. The system of claim 36, wherein the capacitance sensor includes at least one capacitor plate having a non-planer shape.

42. The system of claim 36, wherein the membrane receptacle is part of a disposable set.

43. The system of claim 36, wherein the capacitance sensor comprises first and second capacitor plates and an electrical circuit connected to the plates.

44. The system of claim 36, wherein the pair of capacitor plates have a shape substantially the same as the fluid receptacle when the fluid receptacle is substantially full of fluid.

45. The system of claim 36, wherein the medical fluid delivery system is a dialysis system.

46. The system of claim 45, wherein the dialysis system is a continuous flow peritoneal dialysis system.

47. A dialysis system, comprising:
a fluid flow mechanism having a flexible membrane receptacle arranged to hold and convey a fluid during a dialysis treatment; and
a fluid volume capacitance sensor having first and second capacitor plates each positioned and arranged on an opposing side of the fluid flow mechanism to measure a volume of the fluid conveyed by the flexible membrane receptacle during the dialysis treatment.

48. The dialysis system of claim 47, wherein the fluid flow mechanism is a continuous flow mechanism capable of performing continuous flow dialysis.

49. The dialysis system of claim 47, wherein the fluid flow mechanism is fluidly connected to a peritoneal dialysis catheter.

50. The dialysis system of claim 47, wherein the fluid flow mechanism is fluidly connected to a plurality of peritoneal access lumens.

51. A method of measuring a volume of a medical fluid pumped by a fluid pump, comprising the steps of:
configuring a plurality of capacitor plates to define a space between the plates;
sensing a first state of a medical fluid receptacle located within the space when a flexible membrane receptacle within the medical fluid receptacle is substantially empty of fluid so that a relatively low dielectric fluid exist between the plates and the receptacle;
providing the medical fluid to the flexible membrane receptacle;

sensing a second state of the fluid receptacle with the capacitor plates when the flexible membrane is substantially full of medical fluid; and determining a volume of the medical fluid in the fluid receptacle based on the first and second states sensed by the capacitor plates.

52. The method of claim 51 further comprising the steps of:

substantially emptying the flexible membrane receptacle of fluid; and providing additional medical fluid to the flexible membrane receptacle, sensing another second state, and determining another volume of the medical fluid.

53. The method of claim 51, which includes continuously sensing the state of the flexible membrane receptacle as the fluid enters the fluid receptacle.

54. The method of claim 51, which includes determining a total volume of fluid from a plurality of volumes of medical fluid provided to the flexible membrane receptacle.

55. The method of claim 51, which includes knowing a total amount of medical fluid needed by a patient and stopping the provision of the medical fluid when the total amount has been provided.

56. The method of claim 51, which includes determining a volume of air in the fluid receptacle based on the first and second states sensed by the capacitor plates.

57. A method of providing dialysis to a patient, comprising the steps of:

measuring a volume of dialysis fluid having a sequentially changing inverse relationship with a relatively low dielectric fluid, the dialysis fluid located within a receptacle, the receptacle positioned within a space defined by first and second plates of a capacitance sensor; and pumping a portion of the volume of the dialysis fluid into a portion of a patient using a flexible membrane supported within the receptacle.

58. The method of claim 57, wherein the portion includes a peritoneal cavity of the patient.

59. The method of claim 57, wherein the measuring step further comprises measuring the volume of dialysis fluid in a pump chamber.

* * * * *